US012569530B2

(12) United States Patent
Ahmad et al.

(10) Patent No.: US 12,569,530 B2
(45) **Date of Patent: *Mar. 10, 2026**

(54) TANNIN-BASED ANTIPROLIFERATIVE PHARMACEUTICAL

(71) Applicant: Imam Abdulrahman Bin Faisal University, Dammam (SA)

(72) Inventors: Fazil Ahmad, Dammam (SA); Krishna Mohan Surapaneni, Dammam (SA); Abeer Mohammed Al-Subaie, Dammam (SA); Balu Kamaraj, Dammam (SA)

(73) Assignee: IMAM ABDULRAHMAN BIN FAISAL UNIVERSITY, Dammam (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/646,994

(22) Filed: Apr. 26, 2024

(65) Prior Publication Data

US 2024/0293492 A1 Sep. 5, 2024

Related U.S. Application Data

(62) Division of application No. 17/569,182, filed on Jan. 5, 2022, now Pat. No. 12,318,422.

(51) Int. Cl.

| | |
|---|---|
| ***A61K 36/49*** | (2006.01) |
| ***A23L 33/105*** | (2016.01) |
| ***A61K 31/7024*** | (2006.01) |
| ***A61P 35/00*** | (2006.01) |

(52) U.S. Cl.

CPC ............ *A61K 36/49* (2013.01); *A23L 33/105* (2016.08); *A61K 31/7024* (2013.01); *A61P 35/00* (2018.01)

(58) Field of Classification Search

None

See application file for complete search history.

(56) References Cited

U.S. PATENT DOCUMENTS

| | | | | |
|---|---|---|---|---|
| 5,773,419 | A * | 6/1998 | Falcon | A61K 36/47 514/25 |
| 2008/0175934 | A1 | 7/2008 | Mitra et al. | |
| 2009/0118202 | A1 | 5/2009 | Thekkumkara | |
| 2021/0290647 | A1* | 9/2021 | Gross | A61K 31/7056 |

FOREIGN PATENT DOCUMENTS

| | | | |
|---|---|---|---|
| CN | 109453212 | A | 3/2019 |

OTHER PUBLICATIONS

Masota et al (Molecules 27:5045, 2022) (Year: 2022).*
Nishizawa et al (Chem & Pharmaceut Bull 28:2850-2852, 1980) (Year: 1980).*
Luo et al (J Functional Foods 282-291, 2014) (Year: 2014).*
Emam et al (Journal of Applied Sciences Research 6(7):888-896, 2010) (Year: 2010).*
Winer (Mol Cancer Ther 17:1147-1155, 2018) (Year: 2018).*
Balkrishna et al (Frontiers in Pharmacology, 13:889335 (18 pages), 2022) (Year: 2022).*
Bibi et al (Indian J Pharm Sci 74:375-379, 2012) (Year: 2012).*
Elham, et al. ; A Review of the Phytochemical, Pharmacological, Pharmacokinetic, and Toxicological Evaluation of Quercus Infectoria Galls ; Journal of Ethno-Pharmacology ; Nov. 12, 2020 ; 82 Pages.
Ihn, et al. ; 2-O-digalloyl-1,3,4,6-tetra-O-galloyl-β-D-glucose isolated from Galla Rhois suppresses osteoclast differentiation and function by inhibiting NF-κB signaling ; BMB Rep. 2019; 52(6) ; 409-414 ; 6 Pages.
Jain, et al. ; Role of Quercus infectoria in health and oral health—A Review ; International Journal of Green Pharmacy ; Jul.-Sep. 2019 ; 13(3) ; 6 Pages.
Mohamed et al (J Pesticide Sci 25:410-415, 2000) (Year: 2000).
Mori et al (J Pesticide Sci 25:405-409, 2000) (Year: 2000).

* cited by examiner

*Primary Examiner* — Craig D Ricci
(74) *Attorney, Agent, or Firm* — Oblon, McClelland, Maier & Neustadt, L.L.P.

(57) ABSTRACT

A pharmaceutical composition comprising a tannin selected from 2-O-digalloyl-1,3,4,6-tetra-O-galloyl-β-D-glucose, 3-O-digalloyl-1,2,4,6-tetra-O-galloyl-β-D-glucose, 6-O-digalloyl-1,2,3,4-tetra-O-galloyl-β-D-glucose, 2,6-bis-O-digalloyl-1,3-di-O-galloyl-β-D-glucose, and 6-O-trigalloyl-1,2,3-tri-O-galloyl-β-D-glucose. The tannin may be derived from *Quercus infectoria*. The pharmaceutical composition is used in a method of treating cancer, particularly oral cancer.

9 Claims, 5 Drawing Sheets

TANNIN-BASED ANTIPROLIFERATIVE PHARMACEUTICAL

CROSS-REFERENCE TO RELATED APPLICATIONS

This application is a divisional of U.S. patent application Ser. No. 17/569,182, filed on Jan. 5, 2022.

BACKGROUND OF THE INVENTION

Field of the Invention

The present disclosure relates to a pharmaceutical composition containing an active tannin found in *Quercus infectoria*.

Discussion of the Background

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Cancer cells are known to develop resistance to various chemotherapeutic agents. Natural phytomedicines are currently used for the management of multiple diseases, including cancer. Hence, the use of natural products with medicinal properties that are readily and easily accessible from plant sources for targeting cancer cells is a viable strategy for novel anti-cancer drug development. *Quercus infectoria* (*Q. infectoria*) belongs to the Fagaceae family. This plant is known to contain several bioactive compounds including those with anti-inflammatory and anti-oxidant activity.

Previously, Hasmah et. al., reported the antiproliferative activity of *Q. Infectoria* extracts against the cervical (HeLa) and ovarian (Caov-3) cancer cell lines [Hasmah, A., et. al., Health Environ J., 2010, 1, 2, 17-23]. The ethanolic extract demonstrated a lower $IC_{50}$ value for the HeLa cell line and the aqueous extract a lower $IC_{50}$ value for Caov-3 cell lines. Rehman et. al. reported that *Q. infectoria* is a potent chemopreventive agent and suppresses Fe-NTA-induced renal carcinogenesis, oxidative and inflammatory response in Wistar rats. Chemopreventive effects of *Q. infectoria* were associated with up-regulation of xenobiotic-metabolizing enzyme activities and down-regulation of serum toxicity markers [Rehman, M. U., et al., Int. J. Drug Dev. & Res., 2012, 4, 2, 336-351].

*Q. infectoria* extracts are known to have a wide range of antimicrobial activity against Gram-positive bacterial strains. Studies have also shown good antimicrobial activity of *Q. infectoria* against dental pathogens in both aqueous, acetone and methanolic extracts.

Methanolic extracts of *Q. infectoria* gall have displayed significant analgesic activities in experimental animals. The study conducted on rats has shown that methanolic extracts produced a maximum possible analgesia of 34.2% at 30 min and increased the response time against noxious stimuli similar to opioid analgesics.

The chemical species responsible for this action, however, have not been determined. Identification of the components of *Q. infectoria* and its extracts would allow for the preparation and use of isolates, concentrates, or purified forms of those components. These forms and the use thereof would represent a significant improvement in treating various proliferative disorders.

SUMMARY OF THE INVENTION

The present disclosure relates to a pharmaceutical composition, comprising an active ingredient which is at least one tannin selected from the group consisting of 2-O-digalloyl-1,3,4,6-tetra-O-galloyl-β-D-glucose, 3-O-digalloyl-1,2,4,6-tetra-O-galloyl-β-D-glucose, 6-O-digalloyl-1,2,3,4-tetra-O-galloyl-β-D-glucose, 2,6-bis-O-digalloyl-1,3-di-O-galloyl-β-D-glucose, and 6-O-trigalloyl-1,2,3-tri-O-galloyl-β-D-glucose, or a pharmaceutically acceptable salt, solvate, or prodrug thereof, and a pharmaceutically acceptable carrier and/or excipient, wherein the active ingredient accounts for greater than 75% of a total tannin content of the pharmaceutical composition.

In some embodiments, the active ingredient comprises at least two tannins selected from the group consisting of 2-O-digalloyl-1,3,4,6-tetra-O-galloyl-β-D-glucose, 3-O-digalloyl-1,2,4,6-tetra-O-galloyl-β-D-glucose, 6-O-digalloyl-1,2,3,4-tetra-O-galloyl-β-D-glucose, 2,6-bis-O-digalloyl-1,3-di-O-galloyl-β-D-glucose, and 6-O-trigalloyl-1,2,3-tri-O-galloyl-β-D-glucose, or a pharmaceutically acceptable salt, solvate, or prodrug thereof.

In some embodiments, the active ingredient comprises at least three tannins selected from the group consisting of 2-O-digalloyl-1,3,4,6-tetra-O-galloyl-β-D-glucose, 3-O-digalloyl-1,2,4,6-tetra-O-galloyl-β-D-glucose, 6-O-digalloyl-1,2,3,4-tetra-O-galloyl-β-D-glucose, 2,6-bis-O-digalloyl-1,3-di-O-galloyl-β-D-glucose, and 6-O-trigalloyl-1,2,3-tri-O-galloyl-β-D-glucose, or a pharmaceutically acceptable salt, solvate, or prodrug thereof.

In some embodiments, the active ingredient comprises 6-O-digalloyl-1,2,3,4-tetra-O-galloyl-β-D-glucose, or a pharmaceutically acceptable salt, solvate, or prodrug thereof.

In some embodiments, the active ingredient further comprises at least one tannin selected from the group consisting of 2-O-digalloyl-1,3,4,6-tetra-O-galloyl-β-D-glucose, 3-O-digalloyl-1,2,4,6-tetra-O-galloyl-β-D-glucose, 2,6-bis-O-digalloyl-1,3-di-O-galloyl-β-D-glucose, and 6-O-trigalloyl-1,2,3-tri-O-galloyl-β-D-glucose, or a pharmaceutically acceptable salt, solvate, or prodrug thereof.

In some embodiments, the active ingredient has an estimated binding affinity against MMP-2 of −10.5 to −9.5 to kcal/mol.

In some embodiments, the active ingredient has an estimated binding affinity against NF-κB p65 of −10.5 to −8.7 kcal/mol.

In some embodiments, the active ingredient has an estimated binding affinity against RhoA of −11.0 to −8.8 kcal/mol.

In some embodiments, the pharmaceutically acceptable carrier and/or excipient is at least one selected from the group consisting of a buffer, an inorganic salt, a fatty acid, a vegetable oil, a fatty ester, a surfactant, and a polymer.

In some embodiments, the pharmaceutical composition further comprises one or more of a sweetener, a flavorant, and a colorant.

In some embodiments, the composition is formulated for at least one mode of administration selected from the group consisting of oral administration, parenteral administration, rectal administration, topical administration, transdermal administration, intralesional administration, and inhalation administration.

In some embodiments, the active ingredient is present in an amount of 1 to 75 wt %, based on a total weight of the pharmaceutical composition.

The present disclosure also relates to a method for the treatment of a proliferative disorder in a patient, comprising administering to the patient a therapeutically effective amount of the pharmaceutical composition.

In some embodiments, the proliferative disorder is cancer.

In some embodiments, the cancer is an oral cancer.

In some embodiments, the administering is by oral administration, parenteral administration, rectal administration, topical administration, transdermal administration, intralesional administration, or inhalation administration.

In some embodiments, the therapeutically effective amount of the pharmaceutical composition is from 0.1 to 1000 mg/kg of the active ingredient per body weight of the subject.

In some embodiments, the pharmaceutically acceptable carrier and/or excipient is at least one selected from the group consisting of a buffer, an inorganic salt, a fatty acid, a vegetable oil, a fatty ester, a surfactant, and a polymer.

In some embodiments, the pharmaceutical composition further comprises one or more of a sweetener, a flavorant, and a colorant.

BRIEF DESCRIPTION OF THE DRAWINGS

FIG. 1A shows the binding mode and FIG. 1B shows hydrogen bond and hydrophobic interactions;

FIG. 2A shows the binding mode and FIG. 2B shows hydrogen bond and hydrophobic interactions;

FIG. 3A shows the binding mode and FIG. 3B shows hydrogen bond and hydrophobic interactions;

FIG. 4A shows the binding mode and FIG. 4B shows hydrogen bond and hydrophobic interactions;

FIG. 5A shows the binding mode and FIG. 5B shows hydrogen bond and hydrophobic interactions;

FIG. 6A shows the binding mode and FIG. 6B shows hydrogen bond and hydrophobic interactions;

FIG. 7A shows the binding mode and FIG. 7B shows hydrogen bond and hydrophobic interactions;

FIG. 8A shows the binding mode and FIG. 8B shows hydrogen bond and hydrophobic interactions; FIG. 9A shows the binding mode and FIG. 9B shows hydrogen bond and hydrophobic interactions.

DETAILED DESCRIPTION OF THE INVENTION

Figure 1A:
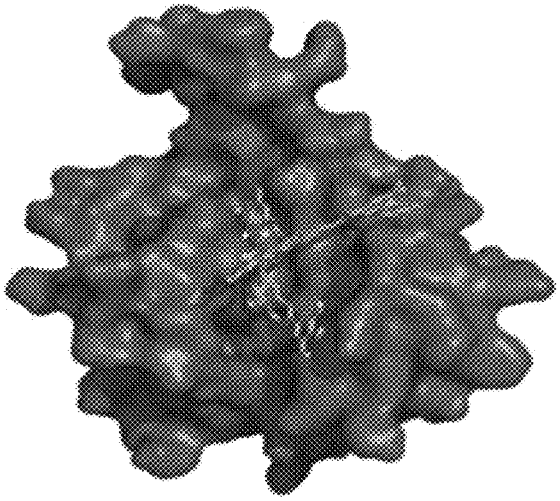
FIGS. 1A-1B depict the interaction of MMP-2 with 6-O-digalloyl-1,2,3,4-tetra-O-galloyl-β-D-glucose, where

In the following description, it is understood that other embodiments may be utilized and structural and operational changes may be made without departure from the scope of the present embodiments disclosed herein.

DEFINITIONS

As used herein the words "a" and "an" and the like carry the meaning of "one or more."

As used herein, the terms "optional" or "optionally" means that the subsequently described event(s) can or cannot occur or the subsequently described component(s) may or may not be present (e.g., 0 wt. %).

As used herein, the terms "compound", "complex", and "product" are used interchangeably, and are intended to refer to a chemical entity, whether in the solid, liquid or gaseous phase, and whether in a crude mixture or purified and isolated.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the disclosure. Many geometric isomers of C═C double bonds, ring systems, and the like can also be present in the compounds, and all such stable isomers are contemplated in the present disclosure. Cis- and trans- (or E- and Z-) geometric isomers of the compounds of the present disclosure are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present disclosure and intermediates made therein are considered to be part of the present disclosure. When enantiomeric or diastereomeric products are prepared, they may be separated by conventional methods, for example, by chromatography, fractional crystallization, or through the use of a chiral agent. Depending on the process conditions the end products of the present disclosure are obtained either in free (neutral) or salt form. Both the free form and the salts of these end products are within the scope of the disclosure. If so desired, one form of a compound may be converted into another form. A free base or acid may be converted into a salt; a salt may be converted into the free compound or another salt; a mixture of isomeric compounds of the present disclosure may be separated into the individual isomers. Compounds of the present disclosure, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the disclosure. Further, a given chemical formula or name shall encompass all conformers, rotamers, or conformational isomers thereof where such isomers exist. Different conformations can have different energies, can usually interconvert, and are very rarely isolatable. There are some molecules that can be isolated in several conformations. For example, atropisomers are isomers resulting from hindered rotation about single bonds where the steric strain barrier to rotation is high enough to allow for the isolation of the conformers. It should be understood that all conformers, rotamers, or conformational isomer forms, insofar as they may exist, are included within the present disclosure.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), and open-chain and cyclic forms of an acetal or hemiacetal (e.g., in reducing sugars).

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomers refer to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. It should be understood that all conformers, rotamers, or conformational isomer forms, insofar as they may exist, are included within the present disclosure.

In terms of the present disclosure, stereoisomers of the ring systems, stereogenic centers, and the like can all be present in the compounds, and all such stable isomers are contemplated in the present disclosure. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g., polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those of ordinary skill in the art.

As used herein, "pharmaceutically acceptable salt" refers to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 18th Edition, Mack Publishing Company, Easton, Pa. (1990), the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, a "composition" or a "pharmaceutical composition" refers to a mixture of an active ingredient(s) with other chemical components, such as pharmaceutically acceptable carriers and/or excipients. One purpose of a composition is to facilitate administration of the active tannins disclosed herein in any of its embodiments to a subject. Pharmaceutical compositions of the present disclosure may be manufactured by processes well known in the art, e.g., by means of conventional mixing, dissolving, granulating, dragee-making, levigating, emulsifying, encapsulating, entrapping or lyophilizing processes. Depending on the intended mode of administration (e.g., oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient" or "active compound", as used herein, refers to an ingredient in the composition that is biologically active, for example, the active tannins described above, a salt thereof, a solvate thereof, a tautomer thereof, a stereoisomer thereof, or any mixtures thereof. In some embodiments, additional therapeutic agents, in addition to the active tannins listed above, may be incorporated into a pharmaceutical composition, for example, a second active ingredient which is chemically distinct from the tannins described above.

As used herein, the phrase "substantially free", unless otherwise specified, describes a particular component being present in an amount of less than about 1 wt %, preferably less than about 0.5 wt %, more preferably less than about 0.1 wt %, even more preferably less than about 0.05 wt %, even more preferably less than about 0.01 wt %, even more preferably less than about 0.001 wt %, yet even more preferably 0 wt %, relative to a total weight of the composition being discussed.

Pharmaceutical Compositions

According to a first aspect, the present disclosure relates to a pharmaceutical composition which comprises an active ingredient and a pharmaceutically acceptable carrier and/or excipient. The active ingredient is at least one tannin selected from the group consisting of 2-O-digalloyl-1,3,4,6-tetra-O-galloyl-β-D-glucose, 3-O-digalloyl-1,2,4,6-tetra-O-galloyl-β-D-glucose, 6-O-digalloyl-1,2,3,4-tetra-O-galloyl-β-D-glucose, 2,6-bis-O-digalloyl-1,3-di-O-galloyl-β-D-glucose, and 6-O-trigalloyl-1,2,3-tri-O-galloyl-β-D-glucose, or a pharmaceutically acceptable salt, solvate, or prodrug thereof. In some embodiments, the active ingredient comprises at least two tannins selected from the above group. In some embodiments, the active ingredient comprises at least three tannins selected from the above group.

In some embodiments, the active ingredient comprises 6-O-digalloyl-1,2,3,4-tetra-O-galloyl-β-D-glucose, or a pharmaceutically acceptable salt, solvate, or prodrug thereof. In some embodiments, the active ingredient further comprises at least one tannin selected from the group consisting of 2-O-digalloyl-1,3,4,6-tetra-O-galloyl-β-D-glucose, 3-O-digalloyl-1,2,4,6-tetra-O-galloyl-β-D-glucose, 2,6-bis-O-digalloyl-1,3-di-O-galloyl-β-D-glucose, and 6-O-trigalloyl-1,2,3-tri-O-galloyl-β-D-glucose, or a pharmaceutically acceptable salt, solvate, or prodrug thereof.

The active ingredient accounts for greater than 75%, preferably greater than 77.5%, preferably greater than 80%, preferably greater than 82.5%, preferably greater than 85%, preferably greater than 87.5%, preferably greater than 90%, preferably greater than 91%, preferably greater than 92%, preferably greater than 93%, preferably greater than 94%, preferably greater than 95%, preferably greater than 96%, preferably greater than 97%, preferably greater than 98%, preferably greater than 99%, preferably greater than 99.5% preferably greater than 99.9% of a total weight of tannins present in the pharmaceutical composition. In some embodiments, the active ingredient accounts for greater than 75%, preferably greater than 77.5%, preferably greater than 80%, preferably greater than 82.5%, preferably greater than 85%, preferably greater than 87.5%, preferably greater than 90%, preferably greater than 91%, preferably greater than 92%, preferably greater than 93%, preferably greater than 94%, preferably greater than 95%, preferably greater than 96%, preferably greater than 97%, preferably greater than 98%, preferably greater than 99%, preferably greater than 99.5% preferably greater than 99.9% of a total number of moles of tannins present in the pharmaceutical composition. This list of tannins will be referred to as "active tannins" in this disclosure. In some embodiments, the active ingredient is substantially free of other tannins. In some embodiments, the pharmaceutical composition is substantially free of other tannins.

In general, the active tannins may be obtained from a suitable plant or plant mixture known to one of ordinary skill in the art. The extract may be made using any suitable part of the plant or plant mixture, including, but not limited to leaves, stems, roots, bark, flowers, fruits, buds, and whole plants. Preferably, the plant is *Quercus infectoria*.

In general, the active tannins may be obtained by any suitable method known to one of ordinary skill in the art. As plants typically contain a wide variety of tannins, a raw or as-obtained extract of a plant such as *Quercus infectoria* may not be suitable for use as the active ingredient. The active ingredient may be concentrated, isolated, purified, or the like from an extract. In general, the extract may be prepared by any suitable method known to one of ordinary skill in the art. Such a method may involve, for example, plant tissue homogenization, soaking, maceration, digestion, decoction, infusion, percolation, Soxhlet extraction, superficial extraction, ultrasound-assisted, microwave-assisted extraction, or any combination thereof. In some embodiments, the plant extract is prepared by soaking. The soaking may be performed at any suitable temperature in which the solvent is a liquid (i.e. from the melting point to the boiling point of the solvent). The soaking may or may not involve agitation, such as shaking or stirring. This soaking may create a plant suspension which comprises a liquid solvent extract and suspended plant solids. In preferred embodiments, the plant solids are removed following the soaking. In general, the plant solids may be removed by any suitable technique known to one of ordinary skill in the art. Examples of such suitable techniques include, but are not limited to decantation, centrifugation, and filtration, but excluding techniques such as evaporation and distillation.

In general, any suitable solvent known to one of ordinary skill in the art may be used to prepare the plant extract. Examples of such suitable solvents include, but are not limited to ethyl acetate, chloroform, dichloromethane, acetone, n-butanol, isopropanol, n-propanol, ethanol, methanol, water, and mixtures thereof. In some embodiments, the solvent comprises water. In preferred embodiments, the solvent is an ethanol and water solution. In some embodiments, the pharmaceutical composition is substantially free of saponins, flavonoids, terpenes, cardenolides, phlobatamins, steroids, and glycosides.

Saponins are a class of plant glycosides in which water-soluble sugars are attached to either a lipophilic steroid or triterpenoid. This hydrophobic-hydrophilic asymmetry means that these compounds have the capacity to lower surface tension and are soap-like, similar to surfactants. Examples of saponins are aescin, araloside A, astragaloside, bacopaside, bacosides I-XI, chaconine, charantin, daucosterol, digitonin, esculeoside A, ginsenoside, glycyrrhizin, gypenoside, A-hederin, holothurin, momordin, osladin, protodioscin, pseudoginsenoside, solanine, and ziziphin.

Flavonoids are a group of naturally occurring polyphenolic compounds characterized by the flavan nucleus structure depicted below.

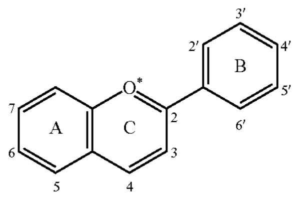

It is worth noting that the phenyl ring labeled "B" in the above image may be connected to either the 2 position as shown or to the 3 position of the "C" ring. Examples of flavonoids include, but are not limited to anthoxanthins, flavans, anthocyanidins, aurones, and chalcones. Examples of anthoxanthins include flavones such as primuletin, chrysin, tectochrysin, primentin, apigenin, acacetin, genkwanin, echioidinin, baicalein, oroxylon, negletein, norwogonin, wogonin, geraldone, tithonine, luteolin, chrysoeriol, diosmetin, pillion, velutin, norartocarpetin, artocarpetin, scutellarein, hispidulin, sorbifolin, pectolinarigenin, cirsimaritin, mikanin, isocutellarein, zapotinin, zapotin, cerrosillin, alnetin, tricin, corymbosin, nepetin, pedalitin, nordifloretin, jaceosidin, cirsiliol, eupatilin, cirsilineol, eupatorin, sinensetin, hypolaetin, onopordin, wightin, nevadensin, xanthomicrol, tangeretin, serpyllin, sudachitin, acerosin, hymenoxin, nobiletin, and scaposin; flavonols such as 3-hydroxyflavone, azaleatin, fisetin, galangin, gossypetin, isorhamnetin, kaempferide, kaempferol, morin, myricetin, natsudaidain, pachypodol, quercetin, rhamnazinm, and rhamnetin; isoflavones such as daidzein, genistein, and orobol; and neoflavonoids such as dalbergichromene, calophyllolide, coutareagenin, dalbergin, and nivetin. Examples of flavans include, but are not limited to flavanols such as catechin, epiafzelechin, fisetinidol, guibourtinidol, mesquitol, robinetinidol, apiforol, and luteoforol; flavan-3,4-diols such as leucocyanidin, leucodelphinidin, leucofisetinidin, leucomalvidin, leucopelargonidin, leucopeonidin, leucorobinetinidin, melacacidin, and teracacidin; flavanones such as blumeatin, butin, eriodictyol, hesperetin, hesperidin, homoeriodictyol, isosakuranetin, naringenin, naringin, pinocembrin, poncirin, sakuranetin, sakuranin, sterubin, and pinostrobin; and flavanonols such as taxifolin, aromadedrin, and engeletin. Examples of an anthocyanidins include, but are not limited to aurantinidin, capensinidin, cyanidin, delphinidin, europinidin, hirsutidin, malvidin, pelargonidin, peonidin, petunidin, pulchellidin, rosinidin, apigeninidin, columnidin, diosmetinidin, luteolinidin, tricetinidin, apigeninidin, and guibourtinidin. Examples of aurones include, but are not limited to aurone, 4'-chloro-2-hydroxyaurone, 4'-chlroaurone, aureusidin, sulfuretin (6,3',4'-trihydroxyaurone), hispidol (6,4'-dihydroxyaurone), and leptosidin. Examples of chalcones include, but are not limited to aurentiacin A, aurentiacin B, 2',6'-dihydroxy-4'-methoxy-3', 5'-dimethyldihydrochalcone, rubone, bakuchalcone, dihydrochalcone, lapathinol, lapathone, brackenin, mixtecacin, 2',6'-dihydroxy-4'-methoxydihydrochalcone, isoliquiritin, licuraside, xanthangelols B through E, ponganone I and II, stipulin, 3,3'-dihydroxychalcone, spinochalcone A, spinochalcone B, flemistrictin A, calythropsin, dihydrocalythropsin, pedicin, fissistin, isofissistin, munchiwarin, prorepensin, lonchocarpin, and cardamonin.

Examples of terpenes include, but are not limited to carotenes such as α-carotene, β-carotene, γ-carotene, δ-carotene, ϵ-carotene, lycopene, neurosporene, phytofluene, and phytoene; and xanthophylls such as canthaxanthin, cryptoxanthin, zeaxanthin, astaxanthin, lutein, rubixanthin.

Examples of cardenolides include, but are not limited to acetyldigitoxins, acetyldigoxins, cymarine, digitoxin, digitoxigenin, digoxigenin, digoxin, medigoxin, neoconvalloside, ouabain, strophanthins, and strophanthidin.

Examples of steroids include, but are not limited to brassinosteroids such as Brassinolide, 28-homobrassinolide, dolicholide, 28-homodolicholide, 28-norbrassinolide, 2-deoxybrassinlide, castasterone,dolichosterone, 2-epicastasterone, 28-nortyphasterol, typhasterol, secasterone, and secasterol, and phytosterols such as β-sitosterol, campesterol, cholesterol, stigmasterol, stigmastanol, ergosterol, lupeol, and cycloartenol.

Glycosides are molecules in which a sugar group is bonded through its anomeric carbon to another group via a glycosidic bond. Glycosides can be linked by an O- (an O-glycoside), N- (a glycosylamine), S- (a thioglycoside), or C- (a C-glycoside) glycosidic bond. A glycosidic bond refers to a bond formed between the hemiacetal or hemiketal group of a saccharide (or a molecule derived from a saccharide) and, in the case of an O-glycosidic bond the oxygen atom of a hydroxyl group of some compound such as an alcohol. In the case of an S-glycosidic bond, the bond is formed with a sulfur atom of a suitable sulfur-containing functional group. In the case of an N-glycosidic bond, the bond is formed with a nitrogen atom of a suitable nitrogen-containing functional group. In the case of a C-glycosidic bond, the bond is formed with a carbon atom. Examples of glycosides include, but are not limited to spinacetin 3-O-β-d-glucopyranosyl(1→6)-[β-d-apiofuranosyl(1→2)]-β-d-glucopyranoside; patuletin 3-O-β-d-(2"feruloylglucopyranosyl)(1→6)-[β-d-apiofuranosyl(1→2)]-β-d-glucopyranoside; spinacetin 3-O-β-d-(2"-p-coumaroylglucopyranosyl)(1→6)-[β-d-apiofuranosyl (1→2)]-β-d-glucopyranoside; spinacetin 3-O-β-d-(2"feruloylglucopyranosyl)(1→6)-[β-d-apiofuranosyl (1→2)]-β-d-glucopyranoside; spinacetin 3-O-β-d-(2"feruloylglucopyranosyl)(1→6)-β-d-glucopyranoside; jaceidin 4'-glucuronide; 5,3',4'-trihydroxy-3-methoxy-6:7-methylenedioxyflavone 4'-glucuronide; 5,4'-dihydroxy-3,3'-dimethoxy-6:7-methylenedioxyflavone 4'-glucuronide; patuletin 3-glucosyl(1→6)-[apiosyl(1→2)] glucoside; and patuletin and spinacetin 3-gentiobiosides.

Tannins, as well as saponins, flavonoids, terpenes, cardenolides, phlobatamins, steroids, and glycosides may be collectively referred to as "phytochemicals".

In general, the concentration, isolation, or purification of the active tannins may be performed by any suitable technique or combination of techniques known to one of ordinary skill in the art. Examples of such techniques include, but are not limited to acid and/or base extraction; precipitation methods such as solvent precipitation, exclusive reagent precipitation (particularly precipitation involving gelatin which may be useful for separating tannins from other phytochemicals), and salting out; dialysis; fractional distillation; crystallization; and chromatographic techniques such as partition chromatography, adsorption chromatography, gel chromatography, ion-exchange chromatography, high performance liquid chromatography (HPLC), and affinity chromatography. In some embodiments, the concentration, isolation, or purification of the active tannins involves the preparation of an alcoholic extract, preferably a methanolic extract. The alcoholic extract may then be partitioned with ethyl acetate to form an ethyl acetate partition. The concentration, isolation, or purification of the active tannins may then involve reverse phase chromatography using a nonpolar adsorbent resin such as Diaion® HP-20 available from Supelco. The reverse phase chromatography preferably involves gradient elution with a water/methanol mixture. Various fractions (e.g. 40% MeOH v/v or 60% MeOH v/v) from the reverse phase chromatography may be subjected to separation by size exclusion chromatography with a suitable size exclusion resin such as Toyopearl® HW-40 and/or YMC-Pack® ODS-AQ 120-50S. The size exclusion chromatography preferably involves gradient elution with methanol. See, for example, Kwon, et. al. [Kwon O. J., et. al., Molecules, 2013, 18, 9, 10629-10638, incorporated herein by reference in its entirety].

As described in detail below, the pharmaceutical compositions of the present disclosure may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) rectal (or vaginal) administration, for example, as a pessary, cream or foam; (5) sublingual administration; (6) ocular administration; (7) transdermal administration; (8) inhalation administration, for example as a dry powder, aerosol, or vapor; or (9) intralesional administration.

In some embodiments, the pharmaceutical composition comprises 0.01 to 99 wt. % of the active tannins relative to a total weight of the pharmaceutical composition. For example, the pharmaceutical composition may contain at least 0.01 wt. %, at least 0.05 wt. %, at least 0.1 wt. %, at least 0.5 wt. %, at least 5 wt. %, at least 10 wt. %, at least 15 wt. %, at least 20 wt. %, at least 25 wt. %, at least 30 wt. %, at least 35 wt. %, at least 40 wt. %, at least 45 wt. %, at least 50 wt. %, at least 55 wt. %, at least 60 wt. %, at least 65 wt. %, at least 70 wt. %, and up to 99 wt. %, up to 98 wt. %, up to 95 wt. %, up to 90 wt. %, up to 85 wt. %, up to 80 wt. %, up to 75 wt. % of the active tannins relative to a total weight of the pharmaceutical composition. In preferred embodiments, the pharmaceutical composition includes 1 to 75 wt. %, preferably 2.5 to 70 wt. %, preferably 5 to 65 wt. %, preferably 7.5 to 60 wt. %, preferably 10 to 50 wt. % of the active tannins, based on a total weight of the pharmaceutical composition.

In some embodiments, the active ingredient of the current disclosure, e.g., the at least one tannin selected from the group consisting of 2-O-digalloyl-1,3,4,6-tetra-O-galloyl-β-D-glucose, 3-O-digalloyl-1,2,4,6-tetra-O-galloyl-β-D-glucose, 2,6-bis-O-digalloyl-1,3-di-O-galloyl-β-D-glucose, and 6-O-trigalloyl-1,2,3-tri-O-galloyl-β-D-glucose, a salt thereof, a solvate thereof, a tautomer thereof, a stereoisomer thereof, or any mixtures thereof, may provide utility as an anticancer agent in reducing the viability of cancer cells derived from human cancer cell lines including, but not limited to, breast cancer cell lines (e.g., MDA-MB-231, MCF-7, SK-BR-3, T47D, VP303); stomach cancer cell lines (e.g., N87, SNU-16, SNU-5, SNU-1, KATO III, AGS); colon/colorectal cancer cell lines (e.g., HCT-116, CACO-2, HT-29, HCT15, MDST8, GP5d, DLD1, SW620, SW403, T84); leukemia cell lines (e.g., HL-60, CESS, CCRF-CEM, CEM/C1, KASUMI-1, ARH-77); liver cancer cell lines (e.g., HepG2, PLC/PRF/5, THLE-3, C3A, SNU-182, SNU-398, SNU-387, SNU-423, SNU-475, SNU-449, and Hep 3B2.1-7); lung cancer cell lines (e.g., A549, NCI-H460, SHP-77, COR-L23/R, NCI-H69/LX20); brain tumor cell lines (e.g., U251); ovarian cancer cell lines (e.g., NCI-ADR/RES, OVCAR-03, A2780, A2780cis, OV7, PEO23); prostate cancer cell lines (e.g., PC-3); renal cancer cell lines (e.g., 786-0); skin cancer or melanoma cell lines (e.g., UACC-62, C32TG, A375, MCC26), and oral cancer cell lines (SCC-180, SCC-9, SCC-90, SCC-152, SCC-154, SCC-15, SCC-25, A-253, FaDu, Detroit 562, CAL 27, UCSF-OT-1109, OEC-M1, BHY, HSC-2, HSC-3, HSC-4, Ca9-22, OC3, HN, ACOSC3, ACOSC4, ACOSC16, ITOC-01, ITOC-02, ITOC-03, and ITOC-04. Preferably, the active ingredient of the pharmaceutical composition of the current disclosure provides utility as an anticancer agent in reducing the viability of cancer cells derived from human oral cancer cell lines (SCC-180, SCC-9, SCC-90, SCC-152, SCC-154, SCC-15, SCC-25, A-253, FaDu, Detroit 562, CAL 27, UCSF-OT-1109, OEC-M1, BHY, HSC-2, HSC-3, HSC-4, Ca9-22, OC3, HN, ACOSC3, ACOSC4, ACOSC16, ITOC-01, ITOC-02, ITOC-03, and ITOC-04).

In some embodiments, the cancer cells are collected from a human patient who is at risk of having, is suspected of having, has been diagnosed with, or is being monitored for recurrence of at least one type of cancer, preferably an oral cancer.

In some embodiments, the ability of the active ingredient to reduce the viability of cancer cells may be determined by contacting the pharmaceutical composition with the cancer cells and then performing cell viability assays. Methods of such assays include, but are not limited to, sulforhodamine-B (SRB) assay, ATP test, Calcein AM assay, clonogenic assay, ethidium homodimer assay, Evans blue assay, 2',7'-dichlorofluorescin diacetate (DCFDA) staining assay, fluorescein diacetate hydrolysis/propidium iodide staining assay, annexin V/fluorescein isothiocyanate (FITC)/propidium iodide staining assay, flow cytometry, Formazan-based assays (MTT, XTT), green fluorescent protein assay, lactate dehydrogenase (LDH) assay, methyl violet assay, propidium iodide assay, Resazurin assay, trypan blue assay, 4',6'-diamidino-2-phenylindole (DAPI) assay, and TUNEL assay, and primary (1°) colonosphere formation assay. In a preferred embodiment, a MTT assay is used. In another preferred embodiment, a Resazurin assay is used.

In some embodiments, additional therapeutic agents in addition to the active tannins of the current disclosure may be incorporated into the pharmaceutical composition. In some embodiments, the pharmaceutical composition includes an additional therapeutic agent that is chemically distinct from the active tannins, such as a chemotherapeutic agent or an anticancer agent, for the treatment or prevention of neoplasm, of tumor or cancer cell division, growth, proliferation and/or metastasis in the subject; induction of death or apoptosis of tumor and/or cancer cells; and/or any other forms of proliferative disorder.

The additional therapeutic agent may be an anticancer agent and may include, but is not limited to, at least one of a mitotic inhibitor; an alkylating agent; an antimetabolite; a cell cycle inhibitor; an enzyme; a topoisomerase inhibitor; a biological response modifier; an anti-hormone; a tubulin inhibitor; a tyrosine-kinase inhibitor; an antiangiogenic agent such as MMP-2, MMP-9 and COX-2 inhibitor; an anti-androgen; a platinum coordination complex (oxaliplatin, carboplatin); a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Exemplary additional therapeutic agents include, but are not limited to, tubulin binding agents including paclitaxel, epothilone, docetaxel, discodermolide, etoposide, vinblastine, vincristine, teniposide, vinorelbine, and vindesine; tyrosine-kinase inhibitors including imatinib, nilotinib, dasatinib, bosutinib, ponatinib, and bafetinib; alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; cytotoxic antibiotics including daunorubicin, doxorubicin, idarubicin, mitomycin, actinomycin, epirubicin; topoisomerase inhibitors including irinotecan, mitoxantrone, topotecan, and mixtures thereof.

As used herein, the phrase "pharmaceutically acceptable carrier and/or excipient" means a pharmaceutically acceptable material, composition or vehicle, such as a liquid or solid filler, carrier, diluent, excipient, manufacturing aid (e.g., lubricant, talc magnesium, calcium or zinc stearate, or steric acid), or solvent encapsulating material, involved in carrying or transporting the subject pharmaceutical composition from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) vegetable oils, such as peanut oil, cottonseed oil, safflower oil, sesame oil, olive oil, com oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations, such as cyclodextrins, liposomes, and micelle forming agents, e.g., bile acids, just to name a few.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the pharmaceutical compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Methods of preparing these pharmaceutical compositions include the step of bringing into association the active ingredient with the pharmaceutically acceptable carrier and/or excipient, and, optionally, one or more accessory ingredients. In general, the compositions are prepared by uniformly and intimately bringing into association one or more active tannins of the present disclosure with liquid carriers, or finely divided solid carriers, or both, and then, if necessary, shaping the product.

Pharmaceutical compositions of the present disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an active tannin as an active ingredient. An active tannin of the present disclosure may also be administered as a bolus, electuary or paste.

In solid dosage forms of the present disclosure for oral administration (capsules, tablets, pills, dragees, powders, granules, troches and the like), the active ingredient is mixed with one or more pharmaceutically acceptable carriers and/or excipients, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants (e.g., fatty acid esters of sorbitan and polyalkolyated fatty acid esters of sorbitan such as TWEEN 80, available from Sigma-Aldrich); (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered pharmaceutical composition moistened with an inert liquid diluent. The tablets, and other solid dosage forms of the pharmaceutical compositions of the present disclosure may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the pharmaceutical composition of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, com, germ, olive, castor and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active tannin(s), may contain suspending agents as, for example, ethoxylated isostearyl alcohols, polyoxyethylene sorbitol and sorbitan esters (including polyoxyethylene fatty acid esters of sorbitan, e.g., TWEEN 80), microcrystalline cellulose, aluminum metahydroxide, bentonite, agar-agar and tragacanth, and mixtures thereof. In preferred embodiments, the pharmaceutical composition is in the form of a suspension, comprising, consisting of, or consisting essentially of the active tannin(s) and the pharmaceutically acceptable carrier and/or excipient, which is preferably a suspending agent (preferably a polyoxyethylene sorbitan ester, preferably a polyoxyethylene fatty acid ester of sorbitan, e.g., TWEEN 80) in an inert diluent (preferably water). Preferably the content of the suspending agent in the suspension ranges from 0.01 to 1 wt. %, preferably 0.05 to 0.8 wt. %, preferably 0.1 to 0.6 wt. %, preferably 0.5 wt. %, based on a total weight of the suspension.

Formulations of the pharmaceutical compositions of the disclosure for rectal or vaginal administration may be presented as a suppository, which may be prepared by mixing the active ingredient with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active tannin(s).

Formulations of the pharmaceutical compositions which are suitable for vaginal administration also include pessaries, tampons, creams, gels, pastes, foams or spray formulations containing such carriers as are known in the art to be appropriate.

Dosage forms for the topical or transdermal administration of a pharmaceutical composition of this disclosure include powders, sprays, ointments, pastes, creams, lotions, gels, solutions, patches and inhalants. The active tannin(s) may be mixed under sterile conditions with a pharmaceutically acceptable carrier, and with any preservatives, buffers, or propellants which may be required.

The ointments, pastes, creams and gels may contain, in addition to an active tannin of this disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active tannin of this disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a pharmaceutical composition of the present disclosure to the body. Such dosage forms can be made by dissolving or dispersing the active tannins in the proper medium. Absorption enhancers can also be used to increase the flux of the active tannin(s) across the skin. The rate of such flux can be controlled by either providing a rate controlling membrane or dispersing the active tannin(s) in a polymer matrix or gel.

Ophthalmic formulations, eye ointments, powders, solutions and the like, are also contemplated as being within the scope of this disclosure.

Pharmaceutical compositions of this disclosure suitable for parenteral administration comprise the active ingredient in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants (e.g., TWEEN 80).

These compositions may also contain adjuvants such as preservatives, wetting agents, emulsifying agents and dispersing agents. Prevention of the action of microorganisms upon the subject pharmaceutical composition may be ensured by the inclusion of various antibacterial and antifungal agents, for example, paraben, chlorobutanol, phenol sorbic acid, and the like. It may also be desirable to include isotonic agents, such as sugars, sodium chloride, and the like into the pharmaceutical compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject pharmaceutical composition in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot injectable formulations are also prepared by entrapping the drug in liposomes or microemulsions which are compatible with body tissue.

In other embodiments, the pharmaceutical composition having the active tannin(s), the salt thereof, the solvate thereof, the tautomer thereof, the stereoisomer thereof, or the mixture thereof has different release rates categorized as immediate release and controlled- or sustained-release.

As used herein, immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to a release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the pharmaceutical composition described herein is not a controlled-release composition.

In one or more embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, but are not limited to, phosphate buffers, citrate buffer, acetate buffers, borate buffers, carbonate buffers, bicarbonate buffers, and buffers with other organic acids and salts.

Exemplary inorganic salts include, but are not limited to, calcium carbonate, calcium phosphate, disodium hydrogen phosphate, potassium hydrogen phosphate, sodium chloride, zinc oxide, zinc sulfate, and magnesium trisilicate.

Exemplary fatty acids include, but are not limited to, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, but are not limited to, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethyl-ammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Therapeutic Applications and Methods

According to a second aspect, the present disclosure relates to a method for treating a proliferative disorder. The method involves administering a therapeutically effective amount of the pharmaceutical composition of the first aspect to a subject.

In some embodiments, the proliferative disorder is cancer. Types of cancers that may be treated with the pharmaceutical composition of this disclosure include, but are not limited to, brain cancers, skin cancers, bladder cancers, ovarian cancers, breast cancers, gastric cancers, pancreatic cancers, prostate cancers, colon/colorectal cancers, blood cancers, lung cancers and bone cancers. In some embodiments, the pharmaceutical composition of this disclosure can be used for the treatment of any cancer type that fails to undergo apoptosis in a patient. This includes, but is not limited to: solid tumors, including but not limited to carcinomas; sarcomas including Kaposi's sarcoma; erythroblastoma; glioblastoma; meningioma; astrocytoma; melanoma; and myoblastoma. Treatment or prevention of non-solid tumor cancers, such as leukemia, is also contemplated by this invention.

Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Bur-kitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse laige B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma. In preferred embodiments, the cancer is an oral cancer.

As used herein, the terms "treat", "treatment", and "treating" in the context of the administration of a therapy to a subject in need thereof refers to the reduction or inhibition of the progression and/or duration of a disease (e.g., cancer), the reduction or amelioration of the severity of the disease, the amelioration of one or more symptoms thereof resulting from the administration of one or more therapies, preventing the disease from occurring in a subject that may be predisposed to the disease but does not yet experience or exhibit symptoms of the disease (prophylactic treatment), slowing or arresting disease development, ameliorating the disease, providing relief from the symptoms or side-effects of the disease (including palliative treatment), and causing regression of the disease. Specific to cancer, and in particular colon or colorectal cancer, these terms may refer to: (1) a stabilization, reduction (e.g., by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g., by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g., colectomy, mastectomy), and (14) preventing or reducing (e.g., by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the compositions according to the present disclosure is desired. In most embodiments, the subject is a mammal, including but not limited to a human, a non-human primate such as a chimpanzee, a domestic livestock such as a cattle, a horse, a swine, a pet animal such as a dog, a cat, and a rabbit, and a laboratory subject such as a rodent, e.g., a rat, a mouse, and a guinea pig. In preferred embodiments, the subject is a human.

The subject may be any subject already with the disease, a subject which does not yet experience or exhibit symptoms of the disease, or a subject predisposed to the disease. In preferred embodiments, the subject is a person who is predisposed to cancer, e.g., a person with a family history of cancer. Women who have (i) certain inherited genes (e.g., mutated BRCA1 and/or mutated BRCA2), (ii) been taking estrogen alone (without progesterone) after menopause for many years (at least 5, at least 7, or at least 10), and/or (iii) been taking fertility drug clomiphene citrate, are at a higher risk of contracting breast cancer. People who (i) consumes a diet high in salty and smoked foods and/or low in fruits and vegetables, (ii) had infection with Helicobacter pylori, and/or (iii) long-term stomach inflammation are at a higher risk of contracting stomach cancer. People who (i) had chemotherapy and radiation therapy for other cancers, (ii) has genetic disorders, such as Down syndrome, and/or (iii) exposure to certain chemicals, such as benzene are at a higher risk of contracting leukemia. People who (i) had inflammatory bowel disease, or a genetic syndrome such as familial adenomatous polyposis (FAP) and hereditary non-polyposis colorectal cancer (Lynch syndrome), and/or (ii) consumes a low-fiber and high-fat diet are at a higher risk of contracting colon cancer. People who (i) are tobacco users, (ii) have been infected with a human papilloma virus (HPV), and (iii) have a genetic disorder, such as Fanconi anemia or Dyskeratosis congenital are at a higher risk of contracting an oral cancer. Any subject with such predispositions, in combination with sound medical judgment, may be candidates for the treatment methods described herein.

In some embodiments, the subject has an oral cancer and is currently undergoing, or has completed one or more chemotherapy regimens. In some embodiments, the subject has been previously administered/treated with, or is being currently administered/treated with, a thymidylate synthase inhibitor (e.g., capecitabine, fluorouracil (5-FU)), a thymidine phosphorylase (TPase) inhibitor (e.g., tipiracil, trifluridine), topoisomerase I inhibitor (e.g., irinotecan), a DNA synthesis inhibitor (e.g., oxaliplatin), and/or a targeted therapy (e.g., cetuximab, bevacizumab, panitumumab, zivaflibercept, ramucirumab). In some embodiments, the subject has been previously administered/treated with, or is being currently administered/treated with, a tubulin binding drug such as paclitaxel, epothilone, docetaxel, discodermolide, etoposide, vinblastine, vincristine, teniposide, vinorelbine, and vindesine, and developed resistance to the tubulin binding drug. In some embodiments, the subject has been previously administered/treated with, or is being currently administered/treated with, a tyrosine-kinase inhibitor such as imatinib, nilotinib, dasatinib, bosutinib, ponatinib, and bafetinib, and developed drug resistance via (i) Bcr-Abl dependent mechanisms involving Bcr-Abl duplication, Bcr-Abl mutation, T315I mutation, and/or P-loop mutations, or (ii) Bcr-Abl Independent mechanisms involving drug efflux caused by P-glycoproteins, drug import by organic cation transporter 1, and/or alternative signaling pathway activation.

The terms "administer", "administering", "administration", and the like, as used herein, refer to the methods that may be used to enable delivery of the active ingredient and/or the pharmaceutical composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed. In preferred embodiments, the active ingredient (e.g., the active tannin) or the pharmaceutical composition described herein are administered orally, preferably as an oral suspension.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", or "pharmaceutically effective amount" refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. Typically, an effective amount of the active tannin(s) to treat cancers such as an oral cancer, in terms of mg of the active tannin(s) per body weight of the subject (kg), ranges from 0.1 to 1,000 mg/kg, preferably 0.5 to 900 mg/kg, preferably 1 to 800 mg/kg, preferably 5 to 750 mg/kg, preferably 10 to 700 mg/kg, preferably 15 to 650 mg/kg, preferably 20 to 600 mg/kg, preferably 50 to 500 mg/kg.

The pharmaceutical composition of the disclosure may be useful for sensitizing cells to apoptotic signals. Thus, in some embodiments, the pharmaceutical composition of the disclosure are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin ortopotecan; (vii) topoisomerase II poisons, (viii) microtubule-directed agents, (ix) kinase inhibitors (x) miscellaneous investigational agents (xi) hormones, (xii) hormone antagonists, and (xii) targeted therapies. It is contemplated that pharmaceutical composition of the disclosure may be useful in combination with any known agents falling into the above 13 classes as well as any future agents that are currently in development. In particular, it is contemplated that pharmaceutical composition of the disclosure may be useful in combination with current Standards of Care as well as any that evolve over the foreseeable future. Specific dosages and dosing regimens would be based on physicians' evolving knowledge and the general skill in the art.

Examples of second therapeutic agents include, but are not limited to, a mitotic inhibitor; an alkylating agent; an antimetabolite; a cell cycle inhibitor; an enzyme; a topoisomerase inhibitor; a biological response modifier; an anti-hormone; a tubulin inhibitor; a tyrosine-kinase inhibitor; an antiangiogenic agent such as MMP-2, MMP-9 and COX-2 inhibitor; an anti-androgen; a platinum coordination complex (oxaliplatin, carboplatin); a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane); a thymidylate synthase inhibitor; a thymidine phosphorylase (TPase) inhibitor; a DNA synthesis inhibitor; and/or a targeted therapy. Exemplary second therapeutic agents include, but are not limited to, tubulin binding agents including paclitaxel, epothilone, docetaxel, discodermolide, etoposide, vinblastine, vincristine, teniposide, vinorelbine, and vindesine; tyrosine-kinase inhibitors including imatinib, nilotinib, dasatinib, bosutinib, ponatinib, and bafetinib; alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; cytotoxic antibiotics including daunorubicin, doxorubicin, idarubicin, mitomycin, actinomycin, epirubicin; topoisomerase inhibitors including irinotecan, mitoxantrone, topotecan; thymidine phosphorylase (TPase) inhibitors such as tipiracil and trifluridine; DNA synthesis inhibitors such as oxaliplatin; targeted therapies such as cetuximab, bevacizumab, panitumumab, zivaflibercept, ramucirumab; and mixtures thereof.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A treatment method may comprise administering the active tannin(s) or a pharmaceutical composition containing the active tannin(s) of the current disclosure in any of its embodiments as a single dose or multiple individual divided doses. In some embodiments, the composition is administered at various dosages (e.g., a first dose with an effective amount of 200 mg/kg and a second dose with an effective amount of 50 mg/kg). In some embodiments, the interval of time between the administration of the pharmaceutical composition and the administration of one or more second therapies may be about 1 to 5 minutes, 1 to 30 minutes, 30 minutes to 60 minutes, 1 hour, 1 to 2 hours, 2 to 6 hours, 2 to 12 hours, 12 to 24 hours, 1 to 2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11 to 15 weeks, 15 to 20 weeks, 20 to 30 weeks, 30 to 40 weeks, 40 to 50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, at least 5 days, at least 6 days, or at least 7 days. In some embodiments, the pharmaceutical composition and optionally one or more second therapies are administered less than 1 day, less than 1 week, less than 2 weeks, less than 3 weeks, less than 4 weeks, less than 1 month, less than 2 months, less than 3 months, less than 6 months, less than 1 year, less than 2 years, or less than 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, at least 10%, at least 15%, at least 20%, at least 25%, at least 30%, at least 40%, at least 50%, at least 60%, at least 70%, at least 75%, at least 80%, at least 85%, at least 90%, at least 95%, at least 99%, or 100%, relative to the tumor size before treatment. In some embodiments, the size of a tumor after treatment is not reduced but is maintained at the same size as before treatment. Methods of assessing tumor size include, but are not limited to, CT scan, MRI, DCE-MRI and PET scan.

The method may further comprise measuring a concentration of a biomarker and/or detecting a mutation in a biomarker before and/or after the pharmaceutical composition comprising the active tannin(s) of the present disclosure is administered. Generic cancer biomarkers include circulating tumor DNA (ctDNA) and circulating tumor cells (CTC). Exemplary biomarkers for colon cancer include, without limitation, carcinoembryonic antigen (CEA), carbohydrate antigen 242 (CA 242), CA 195, CA 19-9, MSI, and 18qLOH. Exemplary biomarkers for breast cancer include, without limitation, BRCA1, BRCA2, HER-2, estrogen receptor, progesterone receptor, cancer antigen 15-3, cancer antigen 27.29, carcinoembryonic antigen, Ki67, cyclin D1, cyclin E, and ERβ. Exemplary biomarkers for stomach cancer include, without limitation, carcinoembryonic antigen (CEA), CA19-9, carbohydrate antigen (CA) 72-4, alpha-fetoprotein, carbohydrate antigen (CA)12-5, SLE, BCA-225, hCG, and pepsinogen I/II.

Potentially predictive cancer biomarkers include, without limitation, mutations in genes BRCA1 and BRCA2 for breast cancer, overexpressions of TYMS, mutations in genes p53 and KRAS for colon cancer, and high concentration levels of AFP, and overexpressions of HSP90a for liver cancer.

The mutation in the biomarker may be detected by procedures such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The concentration level of the cancer biomarker in a sample (i.e., biological sample obtained from the subject in need of therapy including a single cell, multiple cells, fragments of cells, a tissue sample, and/or body fluid, for example red blood cells, white blood cells, platelets, hepatocytes, epithelial cells, endothelial cells, a skin biopsy, a mucosa biopsy, an aliquot of urine, saliva, whole blood, serum, plasma, lymph) may be measured for example by an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, a concentration of the biomarker is measured before and after the administration. When the concentration of the biomarker is maintained, the method may further comprise increasing the effective amount of the active tannin(s) by at least 5%, at least 10%, or at least 30%, and up to 80%, up to 60%, or up to 50% of an initial effective amount. The subject may be administered with the increased dosage for a longer period (e.g., 1 week more, 2 weeks more, or 2 months more) than the duration prescribed with the initial effective amount.

In some embodiments, the administration is stopped once the subject is treated.

The examples below are intended to further illustrate protocols for the characterization, preparation, and use of the pharmaceutical composition and are not intended to limit the scope of the claims.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

EXAMPLES

In-silico studies were carried out to analyze the activity of *Quercus infectoria* against oral cancer. The phytocompounds isolated from *Quercus infectoria* were screened against the targets MMP-2, NF-kB and RhoA. Here, the MMP-2 plays an important role in cancer cell migration and invasion. This NF-kB is the key factor in cancer cell proliferation and survival. Also, inhibition of RhoA leads to the death of tumor cells and decreased metastasis. A virtual screening process was carried out for 35 compounds against the targets MMP-2, NF-kB and RhoA. From the results, 10 best binding energy complexes were selected based on the binding energy (expressed in kcal/mol), hydrogen bond formation and hydrophobic interactions. The electrostatic and non-electrostatic interactions are based on the shape and charge of the binding molecules. Here, the hydrophobic interactions add more binding free energy in a protein-ligand interaction. Usually, if a conformation has more electrostatic interactions has lower non-electrostatic interaction. Then, 10 compounds were subjected to molecular docking, which results in 6-O-digalloyl-1,2,3,4-tetra-O-galloyl-β-D-glucose, a gallotannin which has 1,2,3,4,6-penta-galloyl-β-Dglucose core and polygalloyl groups at C-2, C-3, C-4 and C-6 position have shown the favorable binding affinity against all the three cancer targets.

To analyze the activity of *Quercus infectoria* against oral cancer, the phytocompounds isolated from *Quercus infectoria* were screened against the targets MMP-2, NF-kB and RhoA. These targets were chosen because MMP-2 plays an important role in cancer cell migration and invasion, NF-kB is the key factor in cancer cell proliferation and survival, and inhibition of RhoA leads to the death of tumor cells and decreased metastasis.

A summary of the active site modeled for each target is provided in Table 1 [Feng Y., et. al., BiochimBiophysActa, 2002, 1598, 1-2, 10-23; Kadioglu O., et. al., Anticancer Res., 2015, 35, 5, 2645-50; and Ihara K., et. al., J Biol Chem., 1998, 273, 16, 9656-66—each incorporated herein by reference in its entirety].

TABLE 1

Active sites of the target Proteins

| S. No: | Target | Protein Data Bank ID | Active sites | References |
|---|---|---|---|---|
| 1. | MMP-2 | 1HOV | HIS85, PRO140, LEU83, PHE148, LYS146, ARG149, PHE87, HIS120, HIS124, HIS30, ALA84 and LEU83 | Feng, et. al. |
| 2. | NF-KB p65 | 1VKX | GLN29, ARG30, ARG33, ARG35, TYR36, CYS38, GLU39, LYS122, LYS123, HIS181, ARG187, LYS218, GLN220, LYS221, ARG246, GLN247 | Kadioglu, et. al. |
| 3. | RhoA | 1A2B | TYR34, ASN149, GLU64, ARG176, CYS16, VAL14, CYS20, LYS118 and GLU158 | Ihara, et. al. |

The virtual screening of 35 phytocompounds isolated from *Q. infectoria* against MMP-2, NF-Kb p65 and RhoA targets resulted in the binding affinity of the protein-ligand complex. The best interacting protein-ligand complexes were selected based on the binding affinity. The DBVS of MMP-2 and 35 phytocompounds resulted in the high binding affinity of certain tannin compounds. The tannins 6-O-digalloyl-1,2,3,4-tetra-O-galloyl-β-D-glucose, 2, 6-bis-O-digalloyl-1,3-di-O-galloyl-β-D-glucose and 2-O-digalloyl-1,3,4,6-tetra-O-galloyl-β-D-glucose are having the best binding affinity of −10.1 kcal/mol, −10.0 kcal/mol, and −9.8 kcal/mol, respectively.

The results from the virtual screening are presented in Tables 2-4 below.

TABLE 2

PyRx (AutodockVina) virtual screening results for phytocompounds isolated from *QuercusInfectoria* against MMP-2

| S. No. | Compound Name | Binding affinity (kcal/mol) |
|---|---|---|
| 1. | 6-O-digalloyl-1,2,3,4-tetra-O-galloyl-β-D-glucose | −10.1 |
| 2. | 2,6-bis-O-digalloyl-1,3-di-O-galloyl-β-D-glucose | −10.0 |
| 3. | 2-O-digalloyl-1,3,4,6-tetra-O-galloyl-β-D-glucose | −9.8 |
| 4. | 4-O-digalloyl-1,2,3,6-tetra-O-galloyl-β-D-glucose | −9.7 |
| 5. | 1,2,3,6-tetra-O-galloyl-β-D-glucose | −9.4 |
| 6. | 1,2,3,4,6-penta-O-galloyl-β-D-glucose | −9.2 |
| 7. | 1,3,4,6-tetra-O-galloyl-β-D-glucose | −9.0 |
| 8. | 1,2,6-tri-O-galloyl-β-D-glucose | −9.0 |
| 9. | 6-O-trigalloyl-1,2,3-tri-O-galloyl-β-D-glucose | −9.0 |
| 10. | Propyl gallate | −8.9 |
| 11. | 1,3,6-tri-O-galloyl-β-D-glucose | −8.7 |
| 12. | Isocryptomerin | −8.4 |
| 13. | Ellagic acid | −8.1 |
| 14. | 1,6-di-O-galloyl-O-β-D-glucose | −8.0 |
| 15. | Methyl-betulate | −8.0 |
| 16. | M-di gallic acid | −7.9 |
| 17. | 3-O-digalloyl-1,2,4,6-tetra-O-galloyl-β-D-glucose | −7.9 |
| 18. | P-di gallic acid | −7.7 |
| 19. | Methyl-oleanolate | −7.7 |
| 20. | Nyctanthic acid | −7.5 |
| 21. | B-sitosterol | −7.5 |
| 22. | Castalgin | −7.4 |
| 23. | Roburic acid | −7.2 |
| 24. | Vitamin A | −7.1 |
| 25. | 1-O-galloyl-β-D-glucose | −7.0 |
| 26. | 7-methyl-3-hydroxymethylene-4,5,6,7,8-pentahydroxynaph-thalene | −6.8 |
| 27. | Amentoflavone | −6.7 |
| 28. | Castavaloninic acid | −6.4 |
| 29. | Isocastavaloninic acid | −6.4 |
| 30. | Ethyl gallate | −6.4 |
| 31. | Syringic acid | −6.2 |
| 32. | Gallic acid | −6.1 |

TABLE 2-continued

PyRx (AutodockVina) virtual screening results for phytocompounds isolated from *QuercusInfectoria* against MMP-2

| S. No. | Compound Name | Binding affinity (kcal/mol) |
|---|---|---|
| 33 | Methyl gallate | −6.1 |
| 34. | Vitamin C | −5.3 |

TABLE 3

PyRx (AutodockVina) virtual screening results for phytocompounds isolated from *QuercusInfectoria* against NF-kB p65

| S. No. | Compound Name | Binding affinity (kcal/mol) |
|---|---|---|
| 1. | 6-O-digalloyl-1,2,3,4-tetra-O-galloyl-β-D-glucose | −10.2 |
| 2. | 6-O-trigalloyl-1,2,3-tri-O-galloyl-β-D-glucose | −9.2 |
| 3. | 2,6-bis-O-digalloyl-1,3-di-O-galloyl-β-D-glucose | −9.0 |
| 4. | Propyl gallate | −8.6 |
| 5. | M-di gallic acid | −8.0 |
| 6. | 7-methyl-3-hydroxymethylene-4,5,6,7,8-pentahydroxynaph-thalene | −7.9 |
| 7. | 1-O-galloyl-β-D-glucose | −7.8 |
| 8. | Ellagic acid | −7.7 |
| 9. | 3-O-digalloyl-1,2,4,6-tetra-O-galloyl-β-D-glucose | −7.6 |
| 10. | 4-O-digalloyl-1,2,3,6-tetra-O-galloyl-β-D-glucose | −7.6 |
| 11. | P-di gallic acid | −7.5 |
| 12. | 1,6-di-O-galloyl-O-β-D-glucose | −7.5 |
| 13. | Isocastavaloninic acid | −7.4 |
| 14. | 1,2,3,4,6-penta-O-galloyl-β-D-glucose | −7.4 |
| 15. | Methyl-oleanolate | −7.4 |
| 16. | 1,2,6-tri-O-galloyl-β-D-glucose | −7.3 |
| 17. | Isocryptomerin | −7.3 |
| 18. | 1,3,6-tri-O-galloyl-β-D-glucose | −7.3 |
| 19. | 6-O-digalloyl-1,2,3-tri-O-galloyl-β-D-glucose | −7.2 |
| 20. | 1,3,4,6-tetra-O-galloyl-β-D-glucose | −7.2 |
| 21. | 2-O-digalloyl-1,3,4,6-tetra-O-galloyl-β-D-glucose | −7.2 |
| 22. | Castalgin | −7.2 |
| 23. | Castavaloninic acid | −7.0 |
| 24. | Methyl gallate | −6.8 |
| 25. | Gallic acid | −6.7 |
| 26. | Amentoflavone | −6.7 |
| 27. | Ethyl gallate | −6.6 |
| 28. | 1,2,3,6-tetra-O-galloyl-β-D-glucose | −6.5 |
| 29. | Roburic acid | −6.4 |
| 30. | B-sitosterol | −6.1 |
| 31. | Vitamin C | −6.1 |
| 32. | Syringic acid | −6.1 |
| 33. | Nyctanthic acid | −6.0 |
| 34. | Methyl-betulate | −5.5 |
| 35. | Vitamin A | −5.4 |

TABLE 4

PyRx (AutodockVina) virtual screening results for phytocompounds isolated from *QuercusInfectoria* against RhoA

| S.No. | Compound Name | Binding affinity (kcal/mol) |
|---|---|---|
| 1. | 6-O-digalloyl-l,2,3,4-tetra-O-galloyl-β-D-glucose | −10.6 |
| 2. | 2-O-digalloyl-l,3,4,6-tetra-O-galloyl-β-D-glucose | −9.6 |
| 3. | 3-O-digalloyl-l,2,4,6-tetra-O-galloyl-β-D-glucose | −9.2 |
| 4. | Methyl-oleanolate | −8.7 |
| 5. | Nyctanthic acid | −8.6 |
| 6. | 4-O-digalloyl-l,2,3,6-tetra-O-galloyl-β-D-glucose | −8.6 |
| 7. | Castavaloninic acid | −8.6 |
| 8. | B-sitosterol | −8.3 |
| 9. | Isocastavaloninic acid | −8.3 |
| 10. | 1,2,3,4,6-penta-O-galloyl-β-D-glucose | −8.2 |
| 11. | P-di gallic acid | −7.9 |

TABLE 4-continued

PyRx (AutodockVina) virtual screening results for phytocompounds isolated from *QuercusInfectoria* against RhoA

| S.No. | Compound Name | Binding affinity (kcal/mol) |
|---|---|---|
| 12. | Ellagic acid | −7.8 |
| 13. | M-di gallic acid | −7.8 |
| 14. | 1,6-di-O-galloyl-O-β-D-glucose | −7.6 |
| 15. | 6-O-digalloyl-l,2,3-tri-O-galloyl-β-D-glucose | −7.6 |
| 16. | 6-O-trigalloyl-l,2,3-tri-O-galloyl-β-D-glucose | −7.4 |
| 17. | Vitamin A | −7.2 |
| 18. | Vitamin C | −7.2 |
| 19. | 1-O-galloyl-β-D-glucose | −7.2 |
| 20. | Castalgin | −7.1 |
| 21. | 1,3,4,6-tetra-O-galloyl-β-D-glucose | −7.1 |
| 22. | Gallic acid | −6.9 |
| 23. | 1,3,6--tri-O-galloyl-β-D-glucose | −6.9 |
| 24. | Methyl gallate | −6.9 |
| 25. | Ethyl gallate | −6.8 |
| 26. | Amentoflavone | −6.8 |
| 27. | 7-methyl-3-hydroxymethylene-4,5,6,7,8-pentahydroxynaph-thalene | −6.5 |
| 28. | Syringic acid | −6.2 |
| 29. | 1,2,3,6-tetra-O-galloyl-β-D-glucose | −5.9 |
| 30. | 1,2,6-tri-O-galloyl-β-D-glucose | −5.6 |
| 31. | Isocryptomerin | −4.9 |
| 32. | Roburic acid | −4.4 |
| 33. | 2,6-bis-O-digalloyl-l,3-di-O-galloyl-β-D-glucose | −4.0 |
| 34. | Propyl gallate | −4.2 |
| 35. | Methyl-betulate | −3.5 |

Figure 1B:
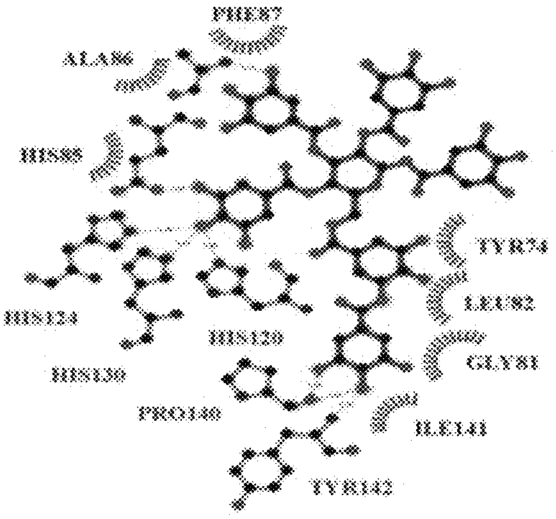
Figure 2A:
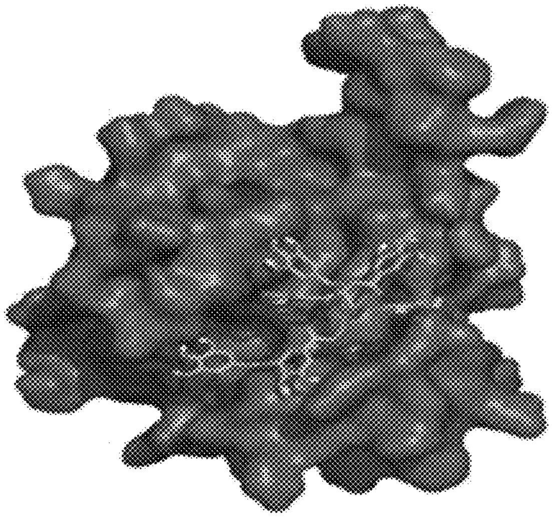
FIGS. 2A-2B depict the interaction of MMP-2 with 2,6-bis-O-digalloyl-1,3-di-O-galloyl-β-D-glucose, where
Figure 2B:
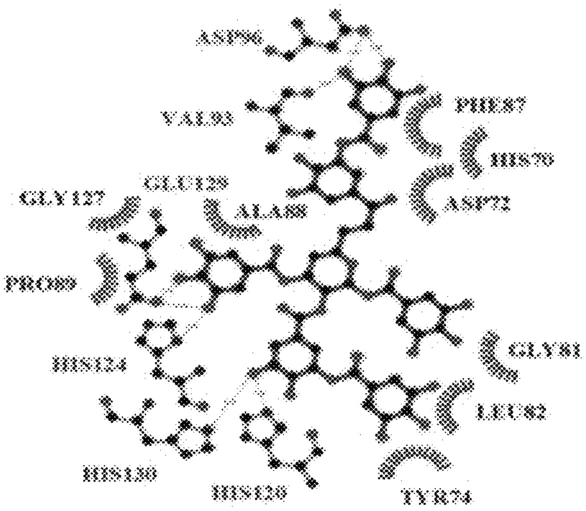
Figure 3A:
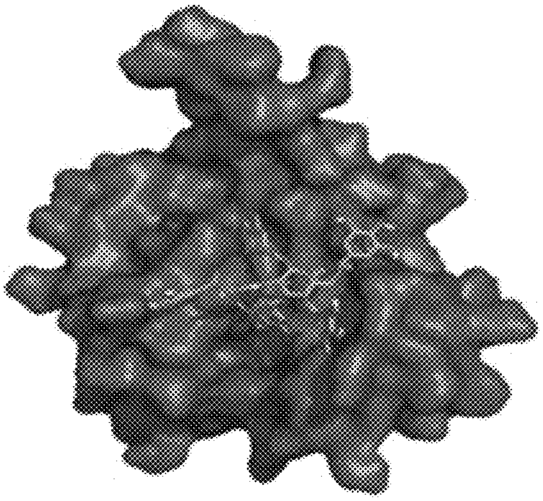
FIGS. 3A-3B depict the interaction of MMP-2 with 2-O-digalloyl-1,3,4,6-tetra-O-galloyl-β-D-glucose, where
Figure 3B:
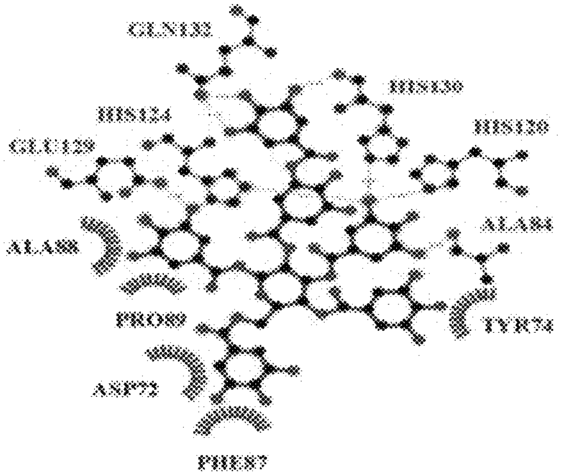

From the virtual screening results, 10 best binding affinity compounds were selected and subjected to molecular docking using AutoDock 4.2.6. For MMP-2 the molecular docking studies revealed 6-O-digalloyl-1,2,3,4-tetra-O-galloyl-β-D-glucose with the high binding affinity of −10.0 kcal/mol, 7 H-bond formations (ALA88, GLU121, HIS120, TYR142, PRO140, HIS130, and HIS124) and 7 hydrophobic interactions (PHE87, ALA86, HIS85, ILE141, GLY81, LEU82, and TYR74). See FIGS. 1A and 1B. Tannin 2,6-bis-O-digalloyl-1,3-di-O-galloyl-β-D-glucose had 6 H-bond formations (ASP96, HIS120, HIS124, GLU129, HIS130, and VAL93) and 8 hydrophobic interactions (PHE87, HIS70, ASP72, GLY81, LEU82, TYR74, PRO89, and GLY127), resulting in a slightly lower binding affinity of −9.8 kcal/mol. See FIGS. 2A and 2B. Tannin 2-O-digalloyl-1,3,4,6-tetra-O-galloyl-β-D-glucose had the most H-bond formations at 8 total (GLN132, HIS124 x2, GLU129, HIS130 x2, HIS120, and ALA84) but only 5 hydrophobic interactions (ALA88, PRO89, TYR74, ASP72, and PHE87), resulting in a binding affinity of −9.4 kcal/mol. See FIGS. 3A and 3B.

The results of the DBVS for MMP-2 are summarized in Table 5 below.

TABLE 5

AutoDock results for MMP-2 and phytocompounds isolated from *QuercusInfectoria*

| S. No: | Compound Name | Binding energy (kcal/mol) | No. of H-bond formation | Amino acid interactions | Hydrophobic interaction |
|---|---|---|---|---|---|
| 1. | 6-O-digalloyl-1,2,3,4-tetra-O-galloyl-β-D-glucose | −10.0 | 7 | ALA88, GLU121, HIS120, TYR142, PRO140, HIS130, and HIS124 | PHE87, ALA86, HIS85, ILE141, GLY81, LEU82, and TYR74 |

TABLE 5-continued

AutoDock results for MMP-2 and phytocompounds isolated from *QuercusInfectoria*

| S. No: | Compound Name | Binding energy (kcal/mol) | No. of H-bond formation | Amino acid interactions | Hydrophobic interaction |
|---|---|---|---|---|---|
| 2. | 2,6-bis-O-digalloyl-1,3-di-O-galloyl-β-D-glucose | −9.8 | 6 | ASP96, HIS120, HIS124, GLU129, HIS130, and VAL93 | PHE87, HIS70, ASP72, GLY81, LEU82, TYR74, PRO89, and GLY127 |
| 3. | 2-O-digalloyl-1,3,4,6-tetra-O-galloyl-β-D-glucose | −9.4 | 8 | GLN132, HIS124, GLU129, HIS130, HIS120, and ALA84 | ALA88, PRO89, TYR74, ASP72, and PHE87 |

Figure 4A:
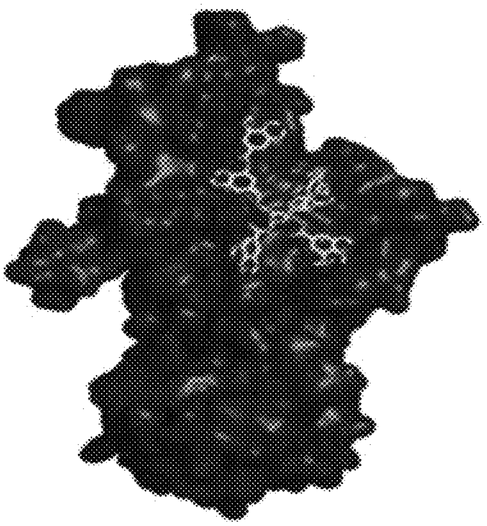
FIGS. 4A-4B depict the interaction of KF-KB p65 with 6-O-digalloyl-1,2,3,4-tetra-O-galloyl-β-D-glucose, where
Figure 4B:
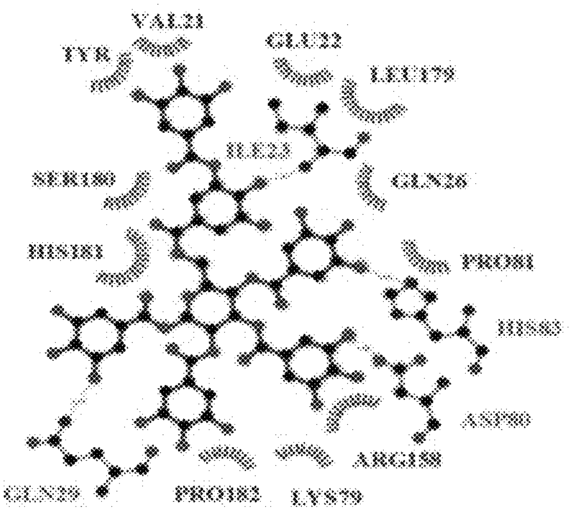
Figure 5A:
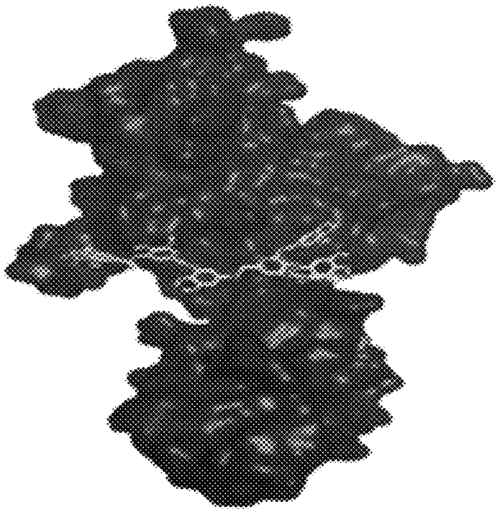
FIGS. 5A-5B depict the interaction of KF-KB p65 with 6-O-trigalloyl-1,2,3-tri-O-galloyl-β-D-glucose, where
Figure 5B:
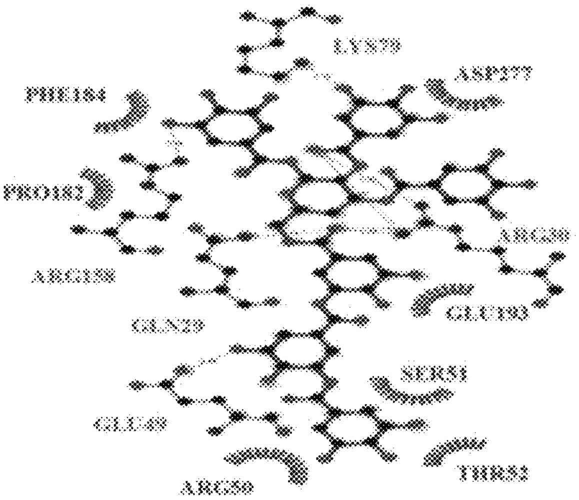
Figure 6A:
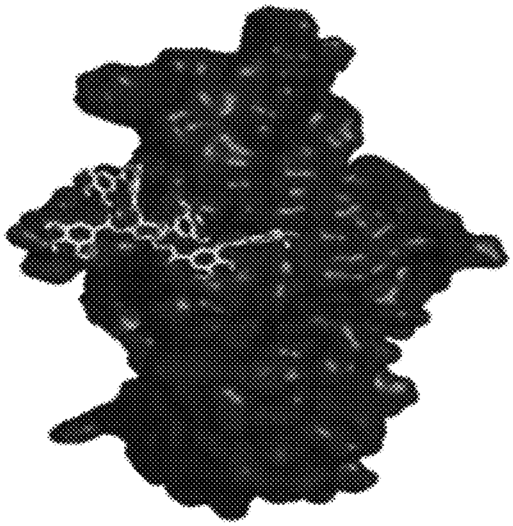
FIGS. 6A-6B depict the interaction of KF-KB p65 with 2,6-bis-O-digalloyl-1,3-di-O-galloyl-β-D-glucose, where
Figure 6B:
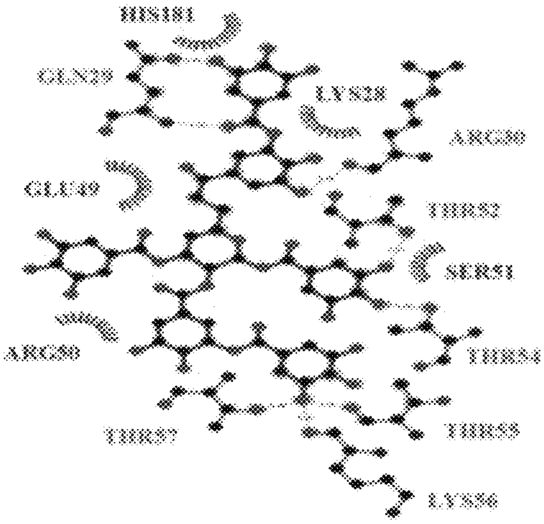

The DBVS of NF-kB p65 against 35 phytocompounds revealed that tannins 6-O-digalloyl-1,2,3,4-tetra-O-galloyl-β-D-glucose, 6-O-trigalloyl-1,2,3-tri-O-galloyl-β-D-glucose and 2,6-bis-O-digalloyl-1,3-di-O-galloyl-β-D-glucose have the high binding affinity of −10.2 kcal/mol, −9.2 kcal/mol, and −9.0 kcal/mol, respectively. The AutoDock results of the 10 best binding affinity compounds revealed the same tannin compounds with the binding energy of 9.8 kcal/mol, 8.8 kcal/mol and 8.5 kcal/mol. The NF-kB p65-6-O-digalloyl-1,2,3,4-tetra-O-galloyl-β-D-glucose complex had 4 H-bond interactions (ILE23, HIS83, ASP80, and GLN29) and 11 hydrophobic interactions (VAL21, TYR20, GLU22, LEU179, GLN26, SER180, HIS181, PRO81, ARG158, LYS79, and PRO182) See FIGS. 4A and 4B. Tannin 6-O-trigalloyl-1,2,3-tri-O-galloyl-β-D-glucose had slightly more H-bond formations at 5 total (LYS79, ARG158, GLN29, GLU49, and ARG30), but only 7 hydrophobic interactions (ASP277, PHE184, PRO182, GLU139, SER51, ARG50, and THR52) resulting in a binding affinity of −8.8 kcal/mol. See FIGS. 5A and 5B. Interestingly, tannin 2, 6-bis-O-digalloyl-1,3-di-O-galloyl-β-D-glucose had the most H-bond formations at 8 (GLN29 x2, ARG30, THR52, THR54, THR55, LYS56, and THR57) but the fewest hydrophobic interactions at 5 (HIS181, GLU49, ARG50, SER51, and LYS28) for a binding affinity of −8.5 kcal/mol. See FIGS. 6A and 6B.

The results of the molecular docking for NF-kB p65 are summarized in Table 6 below.

TABLE 6

AutoDock results for NF-kB p65and phytocompounds isolated from *QuercusInfectoria*

| S. No: | Compound Name | Binding energy (kcal/mol) | No. of H-bond formation | Amino acid interactions | Hydrophobic interaction |
|---|---|---|---|---|---|
| 1. | 6-O-digalloyl-1,2,3,4-tetra-O-galloyl-β-D-glucose | 9.8 | 4 | ILE23, HIS83, ASP80, and GLN29 | VAL21,TYR20, GLU22, LEU179, GLN26, SER180, HIS181, PRO81, ARG158, LYS79, and PRO182 |
| 2. | 6-O-trigalloyl-1,2,3-tri-O-galloyl-β-D-glucose | 8.8 | 5 | LYS79, ARG158, GLN29, GLU49, and ARG30 | ASP277, PHE184, PRO182, GLU139, SER51, ARG50, and THR52 |
| 3. | 2,6-bis-O-digalloyl-1,3-di-O-galloyl-β-D-glucose | 8.5 | 8 | GLN29, ARG30, THR52, THR54, THR55, LYS56, and THR57 | HIS181, GLU49, ARG50, SER51, and LYS28 |

Figure 7A:
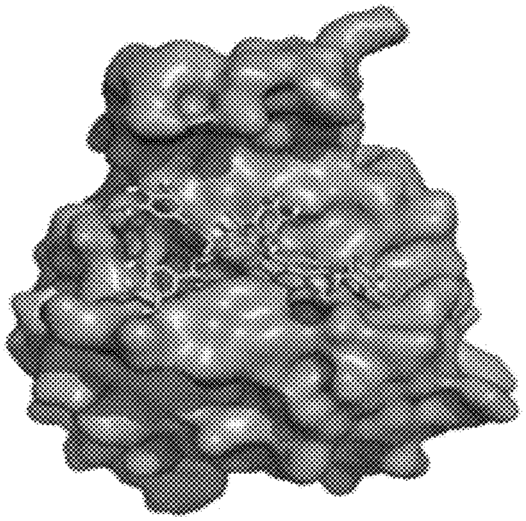
FIGS. 7A-7B depict the interaction of RhoA with 6-O-digalloyl-1,2,3,4-tetra-O-galloyl-β-D-glucose, where
Figure 7B:
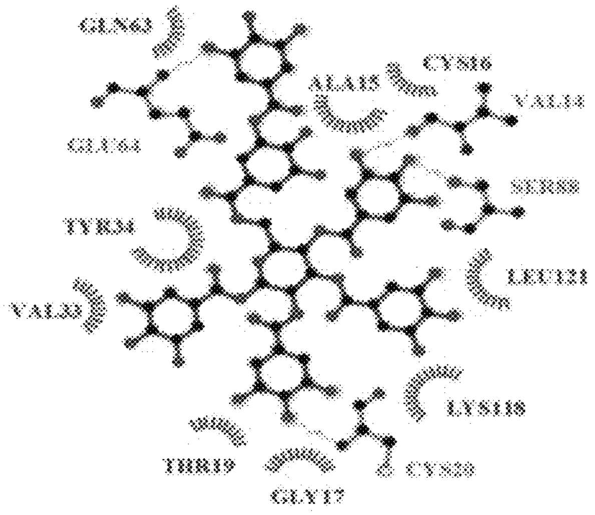
Figure 8A:
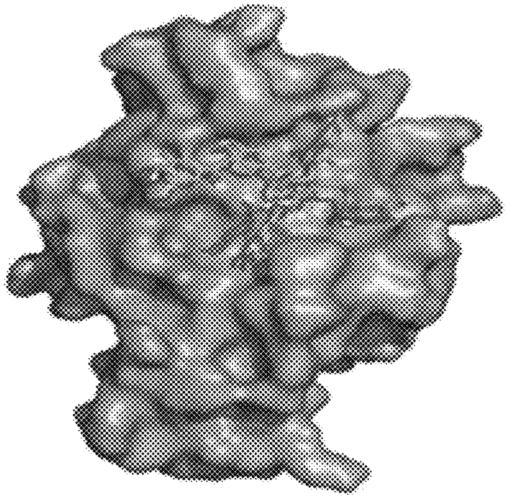
FIGS. 8A-8B depict the interaction of RhoA with 2-O-digalloyl-1,3,4,6-tetra-O-galloyl-β-D-glucose, where
Figure 8B:
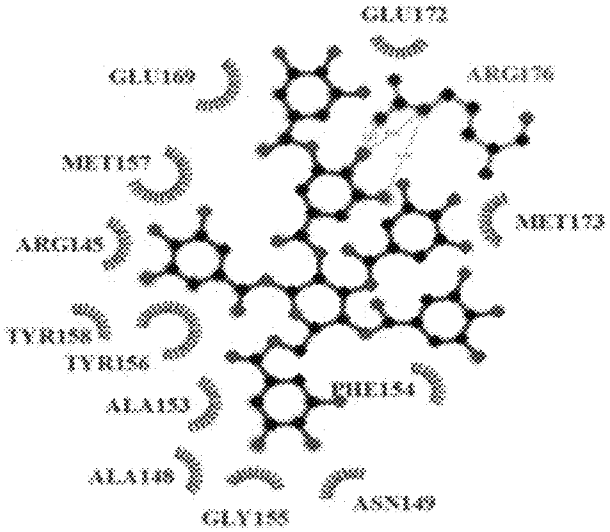
Figure 9A:
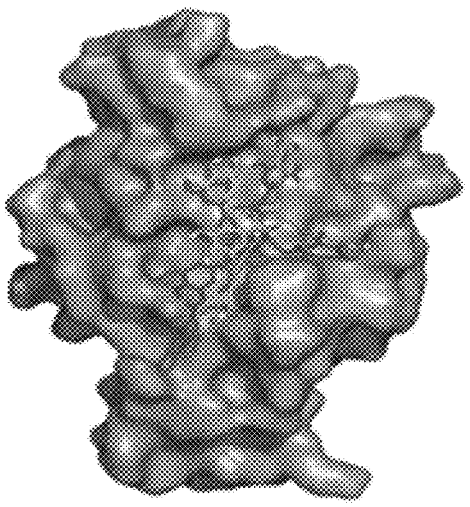
FIGS. 9A-9B depict the interaction of RhoA with 3-O-digalloyl-1,2,4,6-tetra-O-galloyl-β-D-glucose, where
Figure 9B:
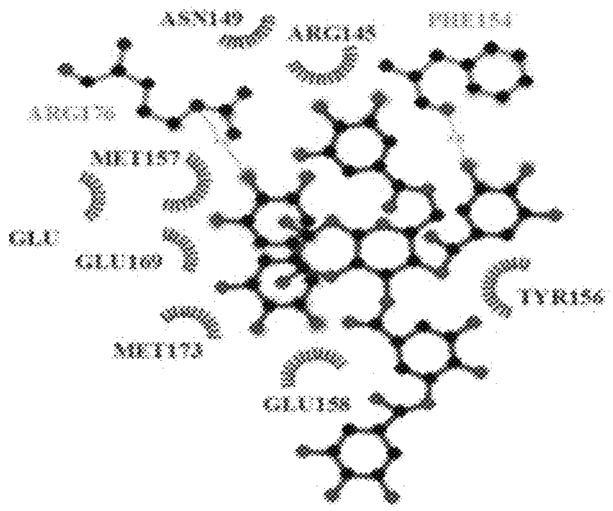

In another DBVS of RhoA and 35 phytocompounds, the best binding affinity was observed for the tannins 6-O-digalloyl-1,2,3,4-tetra-O-galloyl-β-D-glucose, 2-O-digalloyl-1,3,4,6-tetra-O-galloyl-β-D-glucose and 3-O-digalloyl-1,2,4,6-tetra-O-galloyl-β-D-glucose with the binding energy of −10.6 kcal/mol, −9.6 kcal/mol and −9.2 kcal/mol. The AutoDock results of the 10 best compounds reveals the high affinity for the tannins, 6-O-digalloyl-1,2,3,4-tetra-O-galloyl-β-D-glucose (−9.6 kcal/mol), 2-O-digalloyl-1,3,4,6-tetra-O-galloyl-β-D-glucose (−9.0 kcal/mol) and 3-O-digalloyl-1,2,4,6-tetra-O-galloyl-β-D-glucose (−8.8 kcal/mol). Here, the RhoA-6-O-digalloyl-1,2,3,4-tetra-O-galloyl-β-D-glucose complex has 4 H-bond interaction (GLU64, VAL14, SER88, and CYS20) and 9 hydrophobic interactions (GLN63, ALA15, CYS16, TYR34, LEU121, LYS118, VAL33, THR19, and GLY17). See FIGS. 7A-7B. Tannin 2-O-digalloyl-1,3,4,6-tetra-O-galloyl-β-D-glucose had 3 H-bonds, all to ARG176 and 12 hydrophobic interactions (GLU172, GLU169, MET157, ARG145, GLU158, TYR156, ALA153, ALA148, GLY155, ASN149, PHE154, and MET173). See FIGS. 8A-8B. Tannin 3-O-digalloyl-1,2,4,6-tetra-O-galloyl-β-D-glucose had the fewest H-bond interactions with 2 (ARG176 and PHE154) and 8 hydrophobic interactions (ASN149, ARG145, MET157, GLU172, GLU169, MET173, GLU158, and TYR156).

The results of the molecular docking for RhoA are summarized in Table 7 below.

TABLE 7

AutoDock results for RhoA and phytocompounds isolated from *QuercusInfectoria*

| S. No: | Compound Name | Binding energy (kcal/mol) | No. of H-bond formation | Amino acid interactions | Hydrophobic interaction |
|---|---|---|---|---|---|
| 1. | 6-O-digalloyl-1,2,3,4-tetra-O-galloyl-β-D-glucose | −9.6 | 4 | GLU64, VAL14, SER88 and CYS20 | GLN63, ALA15, CYS16, TYR34, LEU121, LYS118, VAL33, THR19, and GLY17 |

TABLE 7-continued

| AutoDock results for RhoA and phytocompounds isolated from *QuercusInfectoria* | | | | | |
|---|---|---|---|---|---|
| S. No: | Compound Name | Binding energy (kcal/mol) | No. of H-bond formation | Amino acid interactions | Hydrophobic interaction |
| 2. | 2-O-digalloyl-1,3,4,6-tetra-O-galloyl-β-D-glucose | −9.0 | 3 | ARG176 | GLU172, GLU169, MET157, ARG145, GLU158, TYR156, ALA153, ALA148, GLY155, ASN149, PHE154, and MET173 |
| 3. | 3-O-digalloyl-1,2,4,6-tetra-O-galloyl-β-D-glucose | −8.8 | 2 | ARG176 and PHE154 | ASN149, ARG145, MET157, GLU172, GLU169, MET173, GLU158, and TYR156 |

The virtual screening and molecular docking of 35 phytocompounds isolated from *Q. infectoria* against the target proteins MMP-2, NF-kB p65 and RhoA reveals that among the 35 phytocompounds, tannins have a favorable binding affinity against the important cancer targets. The comparison of all these docking results reveals that the 6-O-digalloyl-1,2,3,4-tetra-O-galloyl-β-D-glucose, a gallotannin which has 1,2,3,4,6-penta-galloyl-β-Dglucose core and polygalloyl groups at C-2, C-3, C-4 and C-6 position found to have high binding energy with all three cancer targets. The protein-ligand complex is stabilized through the H-bond and hydrophobic interactions. If the hydrophobic interaction is more, there will be less H-bond interaction and vice versa.

The invention claimed is:

1. A method for treating an oral cancer in a patient, comprising administering to the patient a therapeutically effective amount of a pharmaceutical composition, comprising:

an active ingredient which is at least one tannin selected from the group consisting of 2-O-digalloyl-1,3,4,6-tetra-O-galloyl-β-D-glucose, 3-O-digalloyl-1,2,4,6-tetra-O-galloyl-β-D-glucose, 6-O-digalloyl-1,2,3,4-tetra-O-galloyl-β-D-glucose, 2,6-bis-O-digalloyl-1,3-di-O-galloyl-β-D-glucose, and 6-O-trigalloyl-1,2,3-tri-O-galloyl-β-D-glucose, or a pharmaceutically acceptable salt, solvate, or prodrug thereof, and a pharmaceutically acceptable carrier and/or excipient, wherein the active ingredient accounts for greater than 99% of a total weight of tannins present in the pharmaceutical composition.

2. The method of claim 1, wherein the administering is by oral administration, parenteral administration, rectal administration, topical administration, transdermal administration, intralesional administration, or inhalation administration.

3. The method of claim 1, wherein the therapeutically effective amount of the pharmaceutical composition is from 0.1 to 1000 mg/kg of the active ingredient per body weight of the patient.

4. The method of claim 1, wherein the pharmaceutical composition further comprises one or more of a sweetener, a flavorant, and a colorant.

5. The method of claim 1, wherein the active ingredient comprises at least two tannins selected from the group consisting of 2-O-digalloyl-1,3,4,6-tetra-O-galloyl-β-D-glucose, 3-O-digalloyl-1,2,4,6-tetra-O-galloyl-β-D-glucose, 6-O-digalloyl-1,2,3,4-tetra-O-galloyl-β-D-glucose, 2,6-bis-O-digalloyl-1,3-di-O-galloyl-β-D-glucose, and 6-O-trigalloyl-1,2,3-tri-O-galloyl-β-D-glucose, or a pharmaceutically acceptable salt, solvate, or prodrug thereof.

6. The method of claim 1, wherein the active ingredient comprises at least three tannins selected from the group consisting of 2-O-digalloyl-1,3,4,6-tetra-O-galloyl-β-D-glucose, 3-O-digalloyl-1,2,4,6-tetra-O-galloyl-β-D-glucose, 6-O-digalloyl-1,2,3,4-tetra-O-galloyl-β-D-glucose, 2,6-bis-O-digalloyl-1,3-di-O-galloyl-β-D-glucose, and 6-O-trigalloyl-1,2,3-tri-O-galloyl-β-D-glucose, or a pharmaceutically acceptable salt, solvate, or prodrug thereof.

7. The method of claim 1, wherein the active ingredient comprises 6-O-digalloyl-1,2,3,4-tetra-O-galloyl-β-D-glucose, or a pharmaceutically acceptable salt, solvate, or prodrug thereof.

8. The method of claim 7, wherein the active ingredient further comprises 2-O-digalloyl-1,2,3,4-tetra-O-galloyl-β-D-glucose, or a pharmaceutically acceptable salt, solvate, or prodrug thereof.

9. The method of claim 1, wherein the active ingredient comprises 2,6-bis-O-digalloyl-1,3-di-O-galloyl-β-D-glucose, or a pharmaceutically acceptable salt, solvate, or prodrug thereof.

* * * * *